(12) United States Patent
Okamoto (10) Patent No.: US 6,705,866 B1
(45) Date of Patent: Mar. 16, 2004

(54) DENTURE HAVING UNEVEN PATTERNS ON A MUCOSA-FRONTED SURFACE THEREOF AND ITS MANUFACTURING METHOD

(75) Inventor: Shiro Okamoto, Shiga (JP)

(73) Assignee: Casting Okamoto Co., Ltd., Takashima-gun (JP)

( * ) Notice: Subject to any disclaimer, the term of this patent is extended or adjusted under 35 U.S.C. 154(b) by 0 days.

(21) Appl. No.: 09/712,233

(22) Filed: Nov. 15, 2000

Related U.S. Application Data (63) Continuation-in-part of application No. PCT/JP99/06015, filed on Oct. 29, 1999.

(30) Foreign Application Priority Data

Mar. 18, 1999 (JP) ............................................. 11-72825
Mar. 17, 2000 (JP) ............................................. 12-76832

(51) Int. Cl.[7] ........................ A61C 13/20; A61C 13/01; B22C 9/06
(52) U.S. Cl. ................ 433/200.1; 164/DIG. 4
(58) Field of Search ................ 433/200.1, 171, 433/199.1; 164/DIG. 4

(56) References Cited

U.S. PATENT DOCUMENTS

| 287,199 | A | * | 10/1883 | Van Vleck |
| 323,306 | A | * | 7/1885 | Evans |
| 909,038 | A | * | 1/1909 | Telle |
| 1,612,605 | A | * | 12/1926 | Buenaventura |
| 2,392,513 | A | * | 1/1946 | Town |
| 3,083,459 | A | * | 4/1963 | McMurry et al. ........ 433/200.1 |
| 3,657,815 | A | * | 4/1972 | Powell |
| 4,202,098 | A | * | 5/1980 | Russo |
| 4,439,153 | A | * | 3/1984 | Kawahara et al. ....... 433/200.1 |
| 4,824,373 | A | * | 4/1989 | Okada et al. ............ 433/200.1 |

FOREIGN PATENT DOCUMENTS

WO    WO 00/54698    * 9/2000

* cited by examiner

Primary Examiner—Ralph A. Lewis
(74) Attorney, Agent, or Firm—Smith Patent Office (57) ABSTRACT

A denture having a base capable of giving a user a feeling of stability related to the fitting of the denture in the proper oral cavity position. The denture is made by a process comprising the steps of: applying a pattern model onto a shaping surface of a master model. The pattern model making uneven patterns on a mucosa-fronted surface of the base. Next a flexible thin film covers the shaping surface and the pattern model. Thereafter the flexible film and the shaping surface are brought into close contact by evacuating the space between them and pouring an impression material over the flexible thin film.

14 Claims, 5 Drawing Sheets

DENTURE HAVING UNEVEN PATTERNS ON A MUCOSA-FRONTED SURFACE THEREOF AND ITS MANUFACTURING METHOD

CROSS REFERENCE TO RELATED APPLICATIONS

This is a continuation-in-part of International Application PCT/JP99/06015, with an international filing date of Oct. 29, 1999, now pending.

BACKGROUND OF THE INVENTION

1. Field of the Invention

This invention generally relates to a denture for either a maxilla (upper jaw) or a mandible (lower jaw), and more particularly, to a manufacturing method of a denture having uneven patterns on a surface for contact with a mucous membrane (hereinafter called a mucosa-fronted surface). This invention also relates to a refractory model for preparing a metal denture having uneven patterns on its mucosa-fronted surface, and its manufacturing method. This invention further relates to a working model used to prepare a denture of a dental resin having uneven patterns on its mucosa-fronted surface, and a manufacturing method of the working model.

2. Discussion of the Related Art

Dentures involving maxillary and mandibular dentures are prepared based on a positive model of a patient's oral cavity. Mucosa-fronted part of the base of a denture for contact with a mucous membrane, including a gingival surface or gum, is made by using a dental resin or metal. In the pertinent field of industry, dentures are generally classified into metal dentures or dental resin dentures, depending on their materials. When making a denture, a dental technician normally prepares a negative model from a positive model (which may be a direct master model or a replica of the master model). Then, in case of preparing a metal denture, the technician first prepares a refractory model, and next makes a metal base using an appropriate metal material by a known method. In case of preparing a dental resin denture, the technician first prepares a working model from a negative model, and next makes a resin base using an appropriate dental resin material by a known method.

Regarding metal dentures, in recent movements of dental materials from traditional materials like gold and platinum to other metals excellent in biocompatibility, such as Ti alloy, Co—Cr alloy and Mg alloy, for example, metal dentures made using known techniques such as precision casting and lost wax process have been brought into practice. See for example, "Shika Giko Kogaku Rinsho Kenshu Koza 5 (Prosthodontia Clinical Workshop Vol. 5), pp. 121–162, published by Ishiyaku Shuppan Kabushiki Kaisha (Medical, Dental and Pharmaceutical Publication Company). A process of preparing such a metal denture generally includes, for example: preparing a positive model (which is either a master model as a direct replica of a patient's oral cavity or a replica of the master model); imparting the pertinent surface of the positive model (positive surface) onto an impression material such as plaster, agar, silicone, or the like; and next making a copy model (refractory model) by using the impression material after it has been imparted with the pertinent surface. It is empirically known that, in the case of metals having high fusing points, such as a Ti alloy and a Co—Cr alloy, if the texture of the shape-defining surfaces (hereinafter called shaping surfaces) of their molds are rough, problems such as bubbles, blowholes or voids are caused.

Typically, the mucosa-fronted surface of the part of a denture base (including the area for covering a gingival surface or gum) has minute irregularities that are copied from the configuration of the patient's mucous tissues. If the patient's mucous tissues are rough, for example, the shaping surface of a casting mold becomes a roughly irregular plane in the case of, for example a metal denture. Therefore, a denture base made by using the mold results in a still rougher plane on its mucosa-fronted surface due to bubbles produced during the casting process. This results in requiring a great deal of work in the final polishing process.

Taking those problems into account, the inventor proposed a casting method of a casting mold in his Japanese Patent Application No. 7(1995)-315299, laid open as Japanese Laid-Open Publication No. 9(1997)-155505 on Jun. 17, 1997. He also proposed the concept of, prior to taking or imparting the positive surface, i.e. the shaping surface, of a positive mold (master model or a replica of the master model) onto an impression material, putting a thin flexible film over the positive surface, and then bringing the flexible thin film into close contact with the positive surface under a suction force, and thereafter injecting the impression material.

In this novel method, the general contour of the shaping surface transferred to the impression material faithfully traces the positive model. Its surface texture, however, inherits the smooth surface texture of the flexible thin film. As a result, the resultant refractory model having the imprint of the shaping surface transferred from the impression material exhibits a smooth surface texture copied from the surface of the flexible thin film without any influences from the actual configuration of the patient's mucous membrane. Thus it is possible to alleviate the problems of bubbles, blowholes and voids in the casting process and to attain improvements in the final polishing efficiency as well as a significant reduction in the number of defective products.

Having confirmed the excellent effects of that novel technique, the inventor performed further research to proceed with this technique, and has achieved the present invention.

SUMMARY OF THE INVENTION

It is therefore an object of the invention to provide a denture giving a user a feeling of a stable fitting, and a method for fabricating such a denture.

A further object of the invention is to provide a refractory model for preparing a metal denture that can give a user a feeling of a stable fitting, and a method for fabricating such a refractory model.

A still further object of the invention is to provide a working model for preparing a dental resin denture capable of giving a user a feeling of a stable fitting, and a method for fabricating such a working model.

According to the invention, there is provided a method for manufacturing a denture which includes a base having uneven patterns on a mucosa-fronted surface thereof for contact with a person's mucous membrane, comprising the steps of:

providing a shaping surface of a master model or a negative model with a pattern model for making the uneven patterns;

covering the shaping surface bearing the pattern model for the uneven patterns thereon with a flexible thin film;

bringing the flexible thin film into close contact with the model; and pouring a transfer material onto the flexible thin film in close contact with the model and curing the transfer material therein.

The term "uneven patterns" used in this application pertains to any arrangement of a plurality of intentionally embossed, debossed or engraved portions from the standard level forming a land or lands.

Usable as the copying material are plaster, agar, silicone and other known materials. However, plaster is preferably used.

The pattern model for the uneven patterns can be made by, for example, cutting a piece of an appropriate size out of a commercially available netting material, and putting it in contact with the shaping surface of the model. Alternatively, the pattern model for the uneven patterns may be made by selectively coating wax onto the shaping surface of the model. Alternatively, the pattern model of the uneven patterns may be made by bonding a plurality of thin pieces of an appropriate sheet material onto the shaping surface of the model.

These and other features and objects of the invention will become clearer in the light of the following detailed description of the preferred embodiments of the invention described later with reference to the attached drawings listed below.

DETAILED DESCRIPTION OF THE PREFERRED EMBODIMENTS

Figure 1:
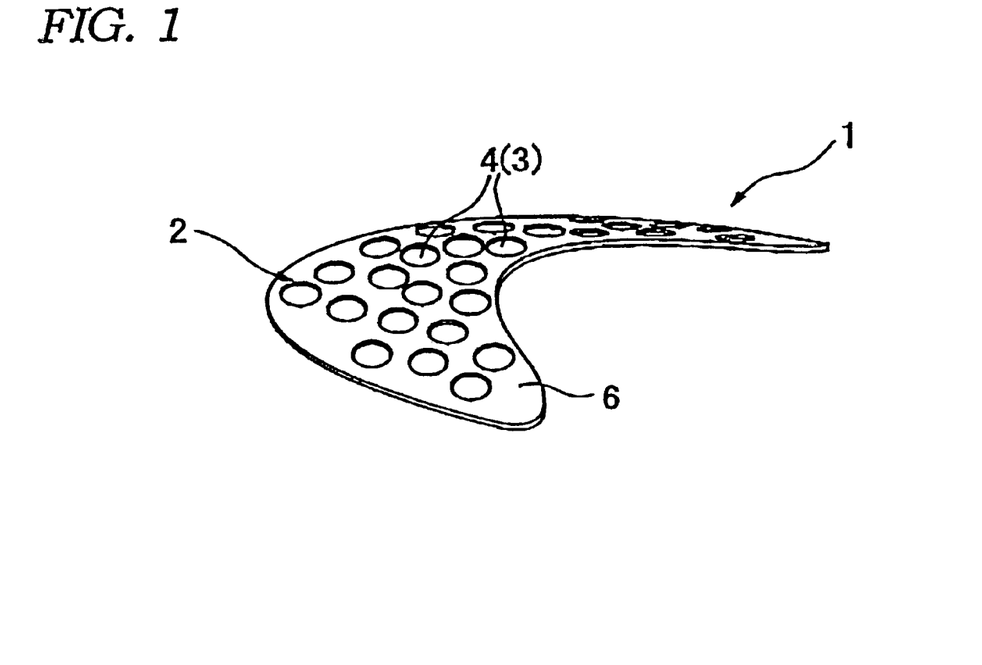
FIG. 1 is a perspective view of a main base portion that is a major part of a base portion (excluding a part thereof covering a gingival surface) of a metal denture according to the present invention.
Figure 2:
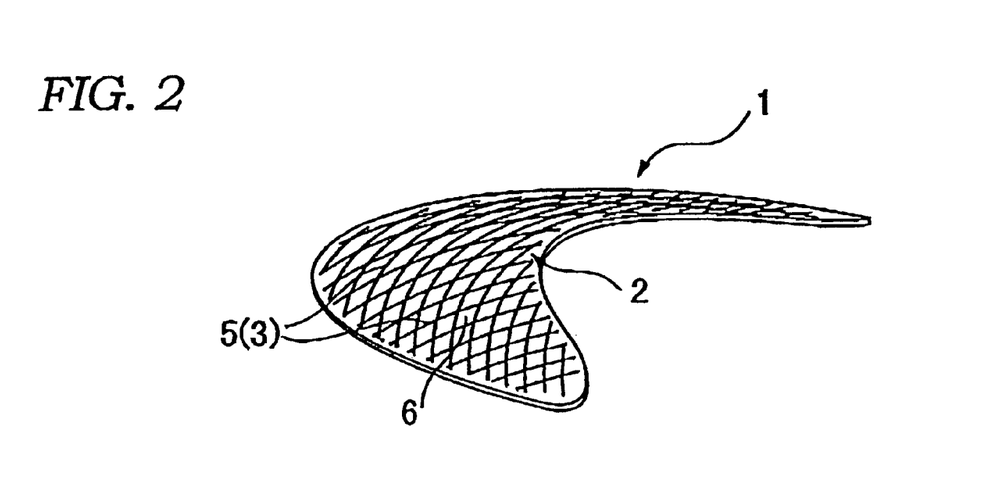
FIG. 2 is a perspective view of a main base portion that is a major part of a base portion (excluding a part thereof covering a gingival surface) of another metal denture according to the present invention.

FIGS. 1 and 2 each illustrate a base of a maxillary metal denture (denture for one's upper jaw) according to the invention. Although the base actually includes a part covering a gingival surface, this part is omitted from the illustration for simplicity. The illustrated base portion 1 is a major part of a denture, which will contact with a central part of the maxilla in one's oral cavity. Its material is not limited to any particular one, but it is recommended that the material be selected from one of the metals having high biocompatibilities, like a Ti alloy, a Co—Cr alloy and a Mg alloy. The base portion 1 includes a mucosa-fronted surface 2 for contact with a central maxillary part of one's oral mucous membrane (not shown), and relatively large uneven patterns are intentionally formed on the mucosa-fronted surface 2. The land or lands 6 appearing among the uneven patterns 3 on the mucosa-fronted surface 2 have a smooth surface texture without inheriting minute irregularities from the person's mucous tissues.

The uneven patterns 3 may be an arrangement of a number of circular depressions 4 separated from one another as shown in FIG. 1, or they may be a network arrangement of elongated grooves 5 as shown in FIG. 2, or alternatively, they may be formed of any combination of these structures. The uneven patterns 3 of the base portion 1 of the metal denture may be spread substantially over the entire area of the mucosa-fronted surface 2, or they may be locally deployed on its right half, left half, gingival surface covering part, or any other local area.

In any of those versions, the shapes of the depressed portions, namely depressions 4 and grooves 5, which make up the uneven patterns 3, as well as lands 6 among these depressed portions, are not restricted to specific structures. However, unlike the minute irregularities copied from a patient's mucous tissues onto conventional metal dentures, the shapes of the depressed portions and lands are intentionally or artificially made in the process of preparing the base portion 1. Their shapes, sizes and depths may be determined as desired, independently from those of the patient's mucous tissues. Therefore, all factors that can characterize the uneven patterns 3, such as the locations of the deployment of the uneven patterns 3 and the shapes and dimensions of the depressions 4 and grooves 5, may be determined as desired to meet individual patients' requests, for example.

A typical way of fabricating the base portion 1 of the denture basically follows a known denture manufacturing method. This includes the process of making a negative model based on a positive model, which is a direct master model of one's maxilla or mandible, or a copy of the master model. Then a copy model (refractory model for a metal denture or working model for a resin denture) is made. For copying the shaping surface of the model, known impression materials such as plaster, agar and silicone, for example, are usable.

A method of fabricating a denture according to the invention is characterized by getting the configuration of the master model, or a copy of the master model (both generally called a master model herein below), by using an impression material (process of making the negative model). Alternatively, the process of making the copy model (refractory model in the case of a metal denture or a working model in the case of a resin denture) from the negative model can be used.

The embodiment shown here takes fabrication of a metal denture as an exemplary way of fabricating a denture according to the invention while employing the method of the invention in the process of making the negative model from the master model. It is more preferable to use the method according to the invention in the step of transferring the surface configuration of the positive model by using an impression material than by using it in the step of making the copy model from the negative model, because the basic contour of the metal denture made in the former case fits the patient's oral cavity better.

FIGS. 3A through 3E are diagrams that illustrate a process of using a positive model to impart its contour to impression materials.

Figure 3A:
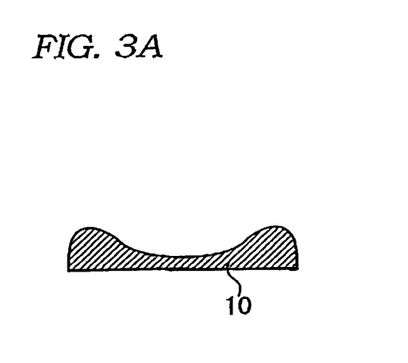
FIGS. 3A through 3E are schematic diagrams that illustrate a process of making an impression model (negative model) from a positive model for making a denture according to the invention.
Figure 3B:
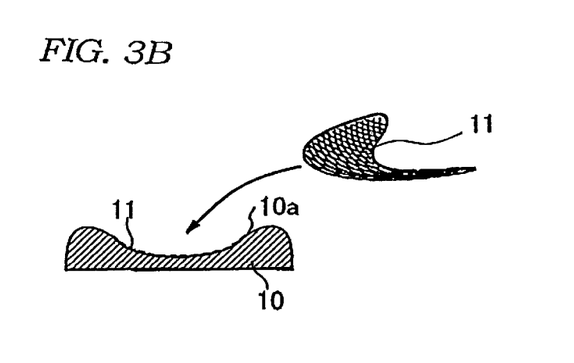

First a positive model 10 (master model) identical to the maxilla of a patient (FIG. 3A) is prepared. Then, a pattern model 11 of uneven patterns 3 is laid over the shaping surface 10a of the positive model 10 (FIG. 3B). The pattern model 11 of the uneven patterns 3 will be explained later in greater detail.

Figure 3C:
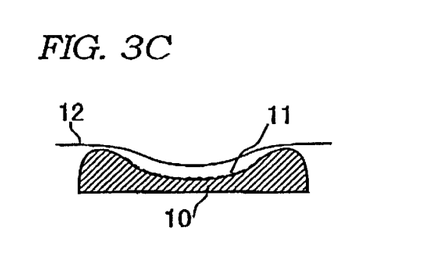
Figure 3D:
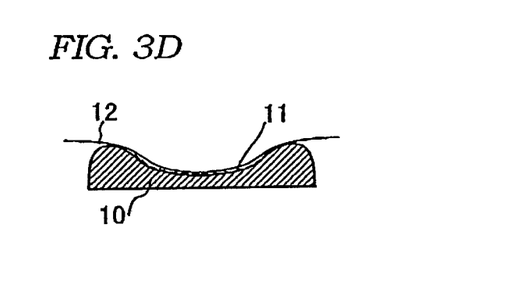

After that, the shaping surface 10a of the positive model 10 is covered with the flexible thin film 12 from above the pattern model 11 of uneven patterns (FIG. 3C). Thereafter, the space between the flexible thin film 12 and the positive model 10 is evacuated to bring them into close contact (FIG. 3D).

Figure 3E:
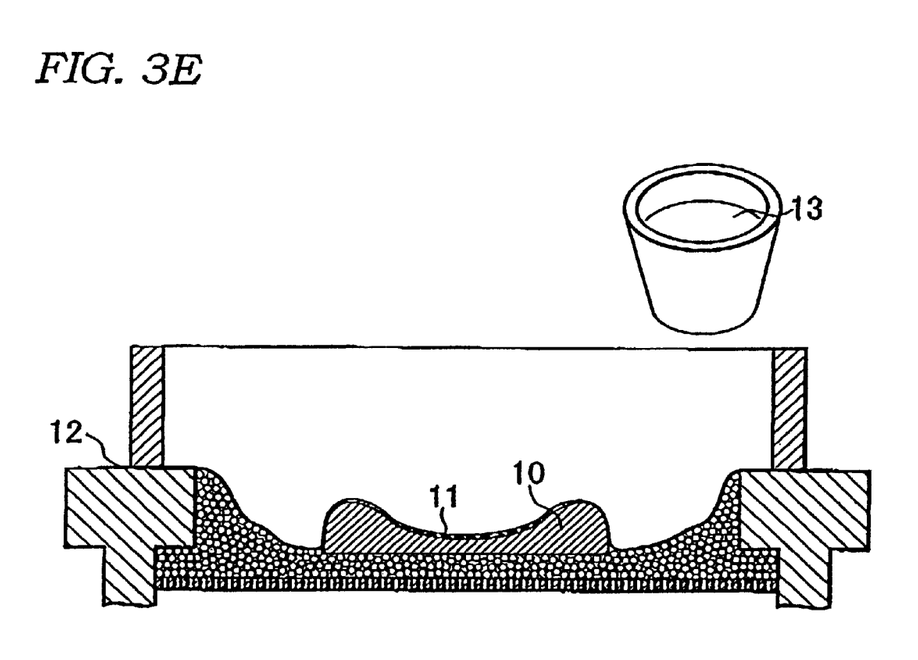

After the flexible thin film 12 is set on the positive model 10, the impression material 13 is poured to impart the shape from the pattern model 11 (FIG. 3E). The impression model, i.e. the negative model, made through the steps shown in FIGS. 3A through 3E, is used for making a refractory model as a casting mold of the metal denture. For actually making the refractory model, a known technique may be used, which is omitted from the explanation of the present application.

Figure 4:
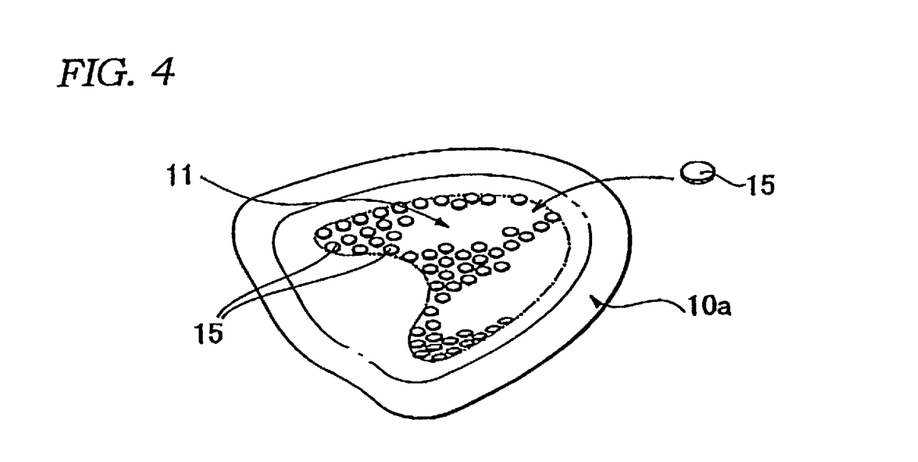
FIG. 4 is a perspective view that illustrates a specific procedure of creating a pattern model of uneven patterns on a shaping surface of a positive model for the purpose of making uneven patterns on a mucosa-fronted surface of the base portion of a denture according to the invention.

The pattern model 11 having uneven patterns 3 is next explained in greater detail with reference to FIGS. 4 through 6. As shown in FIG. 4, the model 11 can be made by cutting a number of thin circular pieces 15 out of vinyl tape coated with an adhesive on one surface thereof, for example, and affixing them onto the shaping surface 10a of the positive model 10 in appropriate intervals. As a result, the pattern model 11 for making the uneven patterns shown in FIG. 1 (circular depressions 4) can be obtained.

Figure 5:
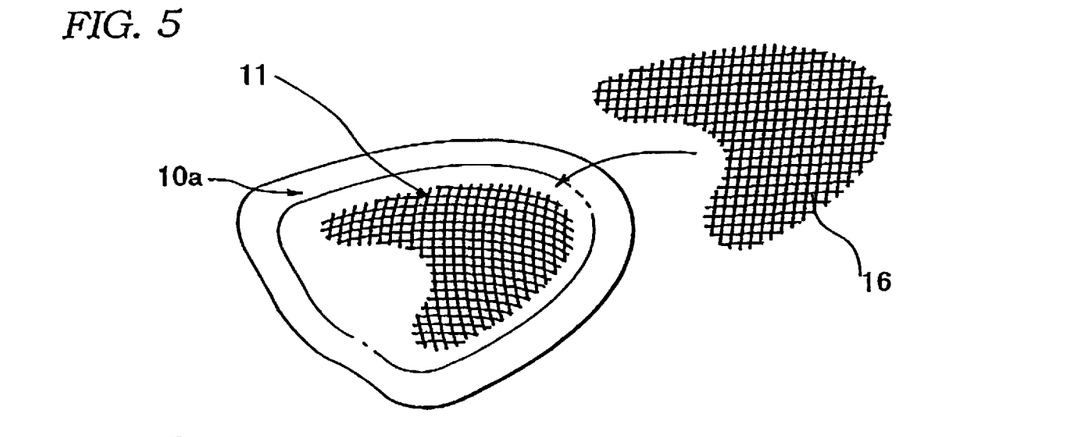
FIG. 5 is a perspective view that illustrates another specific procedure of creating a pattern model of uneven patterns on a shaping surface of a positive model for the purpose of making uneven patterns on a mucosa-fronted surface of the base portion of a denture according to the invention.

Alternatively as shown in FIG. 5, the pattern model 11 may be made by preparing a sheet of netting 16 of an appropriate geometry cut out from commercially available netting knitted from synthetic resin fibers, for example, and affixing it onto the shaping surface 10a of the positive model 10. As a result, it is possible to obtain the pattern model 11 for making the uneven patterns shown in FIG. 2 (the network arrangement of elongated grooves 5) on a metal denture as a final product.

Figure 6:
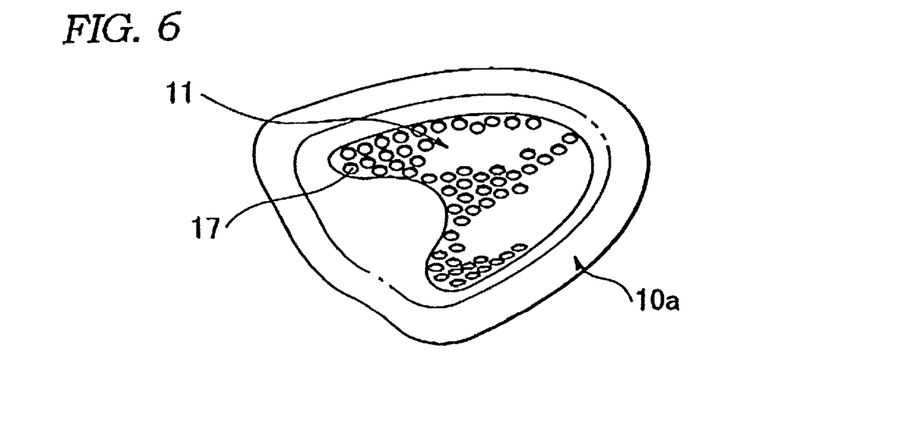
FIG. 6 is a perspective view that illustrates still another specific procedure of creating a pattern model of uneven patterns on a shaping surface of a positive model for the purpose of making uneven patterns on a mucosa-fronted surface of the base portion of a denture according to the invention.

Alternatively as shown in FIG. 6, by coating or bonding drops of wax 17 on the shaping surface 10a of the positive model 10, a pattern model 11 of an appropriate pattern may be made. It will be understood from the above-explained examples that the pattern model 11 for the uneven patterns 3 is made of appropriate selective portions raised from the level of the shaping surface 10a of the positive model artificially and intentionally.

Regarding deployment of the pattern model 11, it may be made to cover substantially the entire area of the shaping surface 10a of the positive model 10 including the part for a gingival surface, or to cover any local area, such as the right half, the left half, or the part for a gingival surface, for example, as understood from the foregoing explanation about the uneven patterns 3. Additionally, the pattern model 11 may be made in the form of a combination of different patterns by locating the netting 16 on a localized area, for example, while coating or bonding drops of the wax 17 in another localized area, for example.

When the netting 16 is used to create the pattern model 11, the dimension of each land 6 in the uneven patterns 3 appearing on the surface 2 of the metal denture is determined by the mesh size. If the netting 16 used has a relatively small mesh size, each land 6 is configured as a slightly tapered projection.

For making a negative model by copying the shaping surface of a positive model via an impression material through the steps explained with reference to FIGS. 3A through 3E, an apparatus proposed by the present inventor in his prior Japanese Patent Application No. 7(1995)-315299 published as Japanese Laid-Open Publication No. 9(1997)-155505 can be used. While incorporating the disclosure of this prior patent application into the present application, that apparatus is outlined below with reference to FIG. 7.

Figure 7:
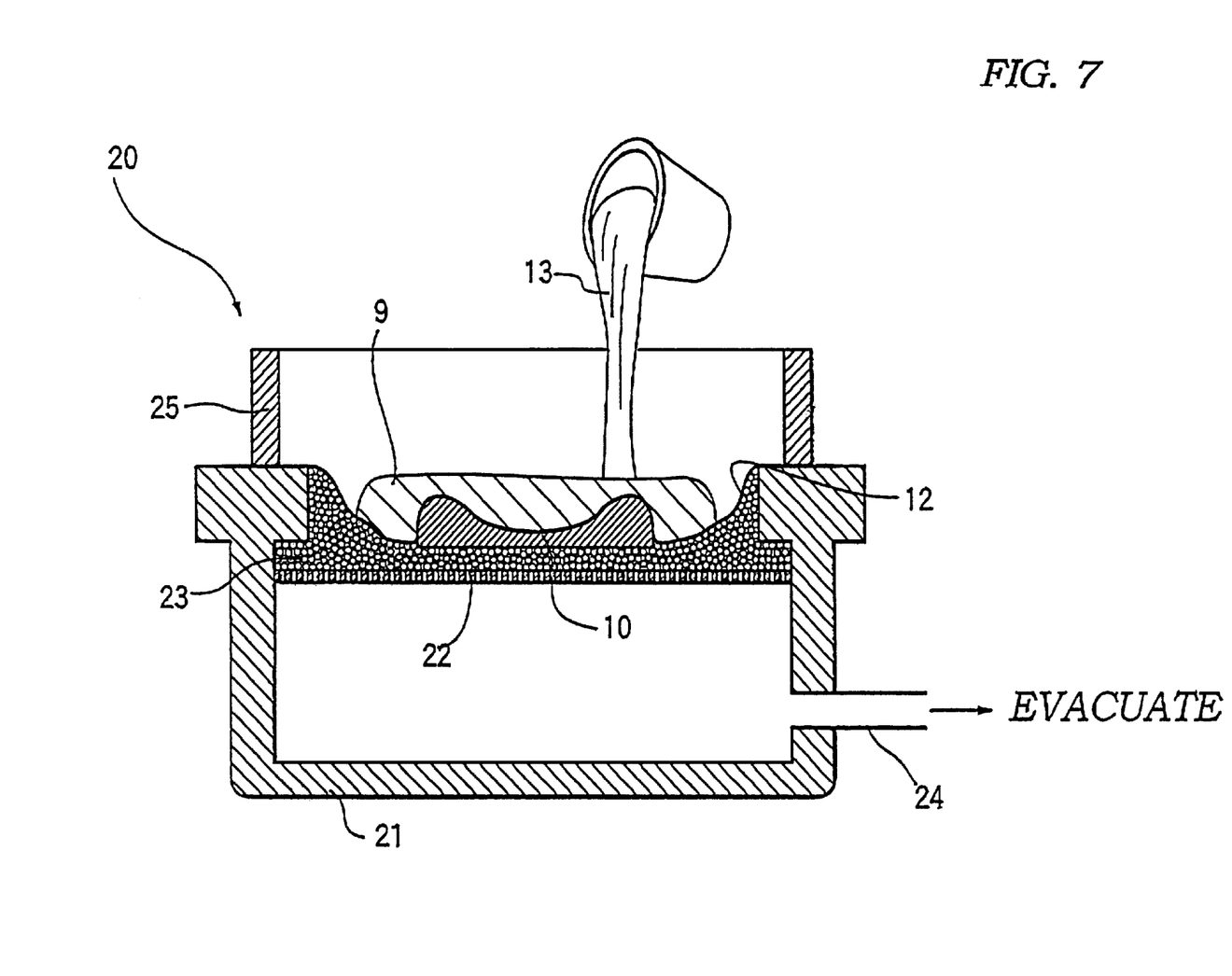
FIG. 7 is a schematic cross-sectional view that shows an apparatus suitable for making a negative model or a copy model used to fabricate a metal denture according to the present invention.

As shown in FIG. 7, the apparatus 20 includes a vessel 21 that is open at an upper area. The vessel 21 is installed with a ventilation partitioning plate 22 supporting numerous small particles 23 thereon. Near the bottom of the vessel 21, a port 24 is formed to communicate with a vacuum source (not shown) such as vacuum pump. For making an impression model, the apparatus 20 is used through the following steps.

(1) A positive model (master model) 10 already having the pattern model 11 with the uneven patterns is put on the small particles 23 (for simplicity, FIG. 7 omits the pattern model 11 from the illustration).

(2) The positive model 10 and the small particles 23 around it are covered with a flexible thin film 12.

(3) A ring member 25 is set on a circumferential area of the flexible thin film 12 to fix it by cooperation with the vessel 21.

(4) The space between the flexible thin film 12 and the positive model 10 is evacuated through the port 24 to bring the flexible thin film 12 into close contact with the positive model 10.

(5) In impression material 13 such as plaster, silicon, or the like, is poured onto the flexible thin film 12.

(6) After the impression material 13 cures, the impression model 9 is removed from the apparatus 20 (completion of the negative model).

The base portion 1 of a denture according to the invention is generally configured to fit a patient's maxilla, but the land or lands 6 of the mucosa-fronted surface 2 have a smooth surface texture copied from the flexible thin film 12 without inheriting the minute irregularities from the patient's mucous tissues. Therefore, it is possible to alleviate the problems of bubbles, blowholes or voids during casting and to attain improvement of the final polishing efficiency and significant reduction of defective products.

Additionally, since the uneven patterns 3 formed on the mucosa-fronted surface 2 of the base portion 1 substantially increases the surface area of the surface 2, contact area between a patient's maxillary mucous membrane and the metal denture can be increased. As a result, the denture gives a feeling of a stable fitting to the patient wearing this denture and provides appropriate stimuli to the maxillary mucous membrane when the patient chews food. In order to give a more deliberate stimuli to the mucous membrane, the land portions 6 made by the uneven patterns 3 are preferably configured as slightly tapered projections. Further, when the invention is applied to a part of the base portion for covering a patient's gingival surface, intentional addition of the uneven patterns stabilizes the denture in position.

As a result of clinical tests using the metal denture, monitored patients gave favorable appraisals related to stability of fit and the uneven patterns 3 stimulated the mucous membrane and promoted salivation, for example.

Although the present invention has been described by way of preferred embodiments, the invention is not limited to exact forms and modes of the embodiments disclosed herein, but also contemplates modifications and variations some of which are listed below.

(1) When the metal denture is fabricated according to the invention, the pattern model 11 of the uneven patterns 3 may be formed on the impression model in the process of making the refractory model (casting model) from the impression model (negative model).

(2) In the case of a dental resin denture according to the invention, the intentional uneven patterns may be made on the shaping surface of the negative model (including the part covering a gingival surface) in the process of making the negative model from the master model by bonding the pattern model 11 onto the master model and adding the evacuating process after covering the pattern model 11 and the master model with the flexible thin film 12, following the above-explained steps. Alternatively, the uneven patterns may be made on the shaping surface of the working model (including the part covering a gingival surface) in the process of making the working model from the negative model by bonding the pattern model 11 onto the negative model and adding the same steps.

(3) When employing the casting method of a casting mold disclosed in Japanese Patent Application No. 7(1995)-315299 (published under Japanese Patent Laid-Open Publication No. 9(1997)-155505), referred to above, to make the metal denture according to the present invention by using a metallic casting mold, the pattern model 11 of the uneven patterns 3 may be formed on a parent model of the surface configuration to be transferred, in the process of making the metallic casting mold from the positive model (master model).

What is claimed is:

1. A method for manufacturing a denture by casting from a copy model copied from a master model via a negative model, the denture including a base having uneven patterns on a mucosa-fronted surface thereof for contact with a mucous membrane, comprising the steps of:

providing a shaping surface of at least one of the master model and the negative model with a pattern model for making the uneven patterns;

covering the shaping surface having the pattern model including the uneven patterns thereon with a flexible thin film;

bringing the flexible thin film into close contact with the at least one master model and negative model via the pattern model; and pouring a transfer material onto the flexible thin film in close contact with the at least one master model and negative model and curing the transfer material therein.

2. The method for manufacturing a denture according to claim 1, wherein the denture is a metal denture.

3. The method for manufacturing a denture according to claim 1, wherein the denture is a dental resin denture.

4. The method for manufacturing a denture according to claim 1, wherein the transfer material is an impression material selected from the group consisting of plaster, agar and silicone.

5. The method for manufacturing a denture according to claim 1, wherein the pattern model for forming the uneven patterns is made of a netting material.

6. The method for manufacturing a denture according to claim 1, wherein the uneven patterns are made by a selective coating of wax on the shaping surface of the at least one master model and negative model.

7. The method for manufacturing a denture according to claim 1, wherein said uneven patterns are made by a plurality of thin pieces attached onto the shaping surface of the at least one master model and negative model.

8. A method for manufacturing a refractory model for a metal denture, the refractory model having uneven patterns on one surface thereof corresponding to a mucosa-fronted surface of the metal denture for contact with a mucous membrane, comprising the steps of:

applying a pattern model having irregular patterns onto a shaping surface of at least one of a master model and a negative model made from the master model;

covering the shaping surface having the pattern model with the uneven patterns thereon with a flexible thin film;

bringing the flexible thin film into close contact with the at least one master model and negative model; and pouring a transfer material onto the flexible thin film in close contact with the at least one master model and negative model and curing the transfer material therein to make up the refractory model.

9. A method for manufacturing a working model for a resin denture, said working model having uneven patterns on one surface thereof corresponding to a mucosa-fronted surface of the resin denture for contact with a mucous membrane, comprising the steps of:

applying a model having irregular patterns onto a shaping surface of at least one of a master model and a negative model made from the master model;

covering the shaping surface having the pattern model with the uneven patterns thereon with a flexible thin film;

bringing the flexible thin film into close contact with the at least one master model and negative model; and pouring a transfer material onto the flexible thin film in close contact with the at least one master model and negative model and curing the transfer material therein to make up the working model.

10. A denture having a nonporous base, comprising:

uneven patterns which are intentionally and artificially made on a mucosa-fronted surface of said base for direct contact with one's mucous membrane without breaking the nonporousness of said base, wherein said base is a metal base.

11. A refractory model of a metal denture, comprising:

uneven patterns intentionally and artificially made on one surface thereof to be imparted onto one surface of a nonporous base of said metal denture for contact with a mucous membrane without breaking the nonporousness of said base.

12. A refractory model of a metal denture, comprising:

uneven patterns intentionally and artificially made on a portion of one surface thereof to be imparted onto a portion of one surface of a nonporous base of said metal denture for contact with a gingival surface without breaking the nonporousness of said base.

13. A method for manufacturing a denture which includes a base having uneven patterns on a mucosa-fronted surface thereof for contact with a mucous membrane, comprising the steps of:

making uneven patterns on a shaping surface of a master model;

covering the shaping surface of the master model including the uneven patterns with a flexible thin film;

bringing the flexible thin film into close contact with the shaping surface of the master model and thereafter pouring a transfer material onto the flexible thin film to make up a negative model;

making a copy model from the negative model; and making the denture from the copy model.

14. A method for manufacturing a denture which includes a base having uneven patterns on a mucosa-fronted surface thereof for contact with a mucous membrane, comprising the steps of:

pouring an impression material onto a master model and thereby making a negative model;

making uneven patterns on a shaping surface of the negative model;

covering the shaping surface of the negative model including the uneven patterns thereon with a flexible film;

bringing the flexible thin film into close contact with the shaping surface of the negative model and thereafter pouring a transfer material onto the flexible thin film to make up a copy model; and making the denture from the copy model.

* * * * *